United States Patent [19]

Liebersohn

[11] 4,371,681

[45] Feb. 1, 1983

[54] BROMINE CONTAINING ALLYLCARBONATES

[76] Inventor: Aaron Liebersohn, Derech Mazada 95, Beer Sheva, Israel

[21] Appl. No.: 316,412

[22] Filed: Oct. 29, 1981

[30] Foreign Application Priority Data

Nov. 21, 1980 [IL] Israel .......................................... 61529

[51] Int. Cl.$^3$ ...................... C08L 85/00; C08L 69/00
[52] U.S. Cl. ................................... 526/295; 526/314; 260/428
[58] Field of Search ................ 526/295, 314; 260/428

[56] References Cited

U.S. PATENT DOCUMENTS

| | | | |
|---|---|---|---|
| 3,497,478 | 2/1970 | Field | 260/77.5 |
| 3,619,260 | 11/1971 | Parker | 117/93.31 |
| 3,666,727 | 5/1972 | Dolinski et al. | 260/77.5 BB |
| 3,679,727 | 7/1972 | Berry et al. | 260/463 |

*Primary Examiner*—Joseph L. Schofer
*Assistant Examiner*—Bernard Lipman
*Attorney, Agent, or Firm*—Toren, McGeady & Stanger

[57] ABSTRACT

There are provided the novel compounds 2,2-bis-(bromomethyl) propane diallyl carbonate and 2,2-bis-(bromomethyl) propane dimethallyl carbonate, a process for the production of these and flame retardant polymers which contain these as flame retardant agents.

7 Claims, No Drawings

BROMINE CONTAINING ALLYLCARBONATES

FIELD OF THE INVENTION

The present invention relates to novel bromine containing allylcarbonate esters. More specifically, it relates to novel flame retarding unsaturated reactive monomers and mainly to 2,2-bis (bromomethyl)propane diallyl or dimethallyl carbonates. A further objective of this invention is to provide flame retardant resins and polymers containing a bromine containing allylcarbonate defined above.

STATE OF THE PRIOR ART

Allylcarbonate esters have been known for some time, and they have found practical utility in preparing polymers possessing excellent impact resistance, scratch resistance, clarity, hardness, infusibility and water resistance in addition to enhanced heat distortion characteristics. U.S. Pat. Nos. 2,592,958, 3,497,478, and 3,770,793 and French Pat. No. 2,278,719 describe such carbonate esters. Recently, there has been a great deal of interest in developing carbonate esters having flame retarding properties. Thus, for example, U.S. Pat. No. 3,688.001 discloses saturated bromine containing neopentyl carbonates for use as additives to impart flame retardance to polyesters such as polyethylene terephthalate.

Chemetron Corp. has disclosed a number of halogen containing carbonate esters as flame retardants in polymers. For example, German Offenlegeschrift No. 2,444,387 describes the saturated Diels-Alder addition product of hexachlorocyclopentadiene and diallyl carbonate which has good fire-proofing properties when used as additive in various polymers. Another publication, German Offenlegeschrift No. 2,444,388 (C.A.83:11345f) discloses ethylene bis (2,3-dibromocyclooctyl carbonate) as flame retarding additive for polypropylene. British Pat. No. 1,442,559 discloses 2,3-dibromopropyl carbonates and flame resistant polymeric compositions containing said carbonate additives.

All of these prior art halogen containing carbonates are saturated materials and thus non-reactive. They are used as additives and do not become part of the polymer or resin matrix.

SUMMARY OF THE INVENTION

The present invention relates to the novel compounds, 2,2-bis (bromomethyl) propane diallyl carbonate and 2,2-bis-(bromomethyl) propane dimethallyl carbonate. These compounds are reactive due to the unsaturated allyl groups and impart excellent permanent flame retardance to polymers and resins.

The compounds of this invention are of the formula:

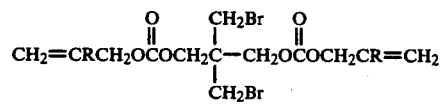

wherein R designates —H or —CH$_3$.

The 2,2-bis (bromomethyl) propane diallyl or dimethallyl carbonate can be prepared in a number of ways:

(a) by reaction of allyl or methallyl alcohol with phosgene and subsequent reaction of the allylchloroformate with 2,2-bis (bromomethyl)-1,3-propane diol;

(b) by reacting 2,2-bis(bromomethyl)-1,3-propane diol with phosgene and subsequently reacting the resulting bischloroformate with allyl or methallyl alcohol;

(c) transesterification of diallyl or dimethallyl carbonate with 2,2-bis (bromomethyl)1,3-propane diol.

These and other methods are well known in the art for preparing carbonate esters having two different alcohol moieties.

The compounds of this invention can be homopolymerized to produce flame resistant resins or they can be copolymerized with other unsaturated monomers to modify the overall resin properties and impart flame retardance to them. For example, the compounds of this invention may be copolymerized with other allyl carbonate esters such as diallyl carbonate or diallyl diglycol or polyglycol carbonate such as CR-39. They may also be polymerized with acrylates, with unsaturated polyesters, with styrenes, with styrene based compounds and with similar compounds.

DESCRIPTION OF THE PREFERRED EMBODIMENT

The following Examples illustrate the invention and are to be construed in a non-limitative manner:

EXAMPLE 1

To a 3-necked flask equipped with a stirrer, thermometer and reflux condenser, was added 362 g. (4.58 moles) pyridine, 350 ml dichloromethane and 500 g 2,2-bis (bromomethyl)-1,3-propane diol. The mixture was stirred until all the diol was dissolved then cooled to 50° C. Allylchloroformate 640 g was added dropwise and the temperature maintained between 5°–15° C. (the reaction was exothermic). The addition was completed after 4½ hours and the reaction mixture was stirred for an additional hour after that at 10° C. To the reaction mixture was added 60 ml aqueous HCl (20%), stirred, and the phases were separated. The organic phase was then washed with 10% aqueous NaCl, treated with activated charcoal and stripped of solvent up to 110° C. at 2–5 mm Hg. The liquid residue was 2,2-bis(bromomethyl)propane diallyl carbonate which was obtained in 94% yield. The compound was identified by IR spectroscopy of the C=O carbonate bond at 1750 cm$^{-1}$ and the C=C allylic double bond at 1650 cm$^{-1}$. Its refractive index was N$_D^{20}$ 1,5009 and the bromine content was 37.0%.

The compound was tested for its effect as reactive flame retarding material in polyester resin as follows.

EXAMPLE 2

A standard polyester alkyd formulation (I) was prepared from 1.935 moles propylene glycol, 0.236 moles diethylene glycol, 1 mole phthalic anhydride and 1 mole maleic anhydride. To this alkyd was added 100 ppm. hydroquinone inhibitor.

To 200 g of the alkyd (I) in a resin kettle heated to 140° C. was added 92.5 g 2,2-bis (bromomethyl)1,3-propane diallyl carbonate with stirring. The mixture was cooled to room temperature and 3% benzoyl peroxide was added. The mixture was then case into a 3 mm thick sheet and cured in an oven at 60° C. for 1 hour, at 70° C. for another hour, and at 90° C. for a further 30 minutes.

The cured sheet was clear and transparent and had a Barcol hardness of 40 with a LOI of 27.

EXAMPLE 3

Similarly, a blend of 155 g of Alkyd (I) and 145 g 2,2-bis(bromomethyl) 1,3-propane diallyl carbonate were cured as in the previous example. The product was a clear, transparent sheet having a Barcol hardness of 40 and a LOI of 28.

EXAMPLE 4

To 100 g of a mixture of Example 3 was added 6.2 g antimony trioxide and thoroughly mixed. This composition was cured in the same manner as Example 2 with the resulting sheet having a Barcol hardness of 40–45 and an LOI of 37.7.

EXAMPLE 5

In a manner similar to Example 1, 2,2-bis(-bromomethyl) 1,3-propane dimethallyl carbonate was prepared using methallyl-chloroformate instead of allyl-chloroformate. The desired product was obtained in 92% yield and identified by its IR absorption for the C=O and allylic double bonds. Its bromine content was 35.1%. It gave similar results as indicated in Examples 2, 3 and 4, when similar compositions were prepared.

I claim:

1. Compounds of the formula

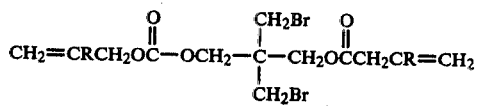

wherein R is —H or —CH$_3$.

2. 2,2-bis-(bromomethyl) propane diallyl carbonate.

3. 2,2-bis-(bromomethyl) propane dimethallyl carbonate.

4. A flame retardant composition comprising the polymerization reaction product of a compound according to claim 1 with a suitable monomer.

5. A composition according to claim 4, wherein the monomer is an unsaturated polyester.

6. A composition according to claim 4, wherein the monomer is an acrylate, a styrene or styrene-based compound or an allyl carbonate ester.

7. A flame retardant composition which is a homopolymer or a copolymer of a compound defined in claim 1.

* * * * *